United States Patent
Long et al.

(10) Patent No.: US 11,193,024 B2
(45) Date of Patent: Dec. 7, 2021

(54) AZO DYE FOR WATERLESS DYEING OF NATURAL FIBERS IN SUPERCRITICAL $CO_2$ FLUID, AND PREPARATION METHOD THEREOF

(71) Applicants: SOOCHOW UNIVERSITY, Suzhou (CN); JIANGSU DANMAO TEXTILE CO., LTD., Jiangsu (CN); NANTONG TEXTILE AND SILK INDUSTRIAL TECHNOLOGY RESEARCH INSTITUTE, Jiangsu (CN)

(72) Inventors: Jiajie Long, Suzhou (CN); Kai Yan, Suzhou (CN); Dao Xu, Suzhou (CN); Jinlin Yu, Suzhou (CN)

(73) Assignees: SOOCHOW UNIVERSITY, Suzhou (CN); JIANGSU DANMAO TEXTILE CO., LTD., Danyang (CN); NANTONG TEXTILE AND SILK INDUSTRIAL TECHNOLOGY RESEARCH INSTITUTE, Nantong (CN)

( * ) Notice: Subject to any disclaimer, the term of this patent is extended or adjusted under 35 U.S.C. 154(b) by 552 days.

(21) Appl. No.: 16/319,190

(22) PCT Filed: Nov. 23, 2018

(86) PCT No.: PCT/CN2018/117077
§ 371 (c)(1),
(2) Date: Jan. 18, 2019

(87) PCT Pub. No.: WO2020/048018
PCT Pub. Date: Mar. 12, 2020

(65) Prior Publication Data
US 2021/0332245 A1 Oct. 28, 2021

(30) Foreign Application Priority Data
Sep. 3, 2018 (CN) .......................... 201811019400.1

(51) Int. Cl.
| | |
|---|---|
| *C09B 62/085* | (2006.01) |
| *D06P 1/382* | (2006.01) |
| *C07C 245/08* | (2006.01) |
| *C07D 251/44* | (2006.01) |
| *D06P 1/94* | (2006.01) |

(52) U.S. Cl.
CPC .......... *C09B 62/085* (2013.01); *C07C 245/08* (2013.01); *C07D 251/44* (2013.01); *D06P 1/382* (2013.01); *D06P 1/94* (2013.01); *C07C 2601/16* (2017.05)

(58) Field of Classification Search
None
See application file for complete search history.

(56) References Cited

FOREIGN PATENT DOCUMENTS

| CN | 104016880 A | 9/2014 |
|---|---|---|
| CN | 105440726 A | 3/2016 |
| GB | 2267095 A | 11/1993 |
| WO | 2017028307 A1 | 2/2017 |

*Primary Examiner* — Joseph R Kosack
(74) *Attorney, Agent, or Firm* — SZDC Law PC

(57) ABSTRACT

The invention discloses a special-purpose reactive disperse dye for waterless dyeing of natural fibers in supercritical $CO_2$ fluid and an intermediate thereof. The reactive disperse dye has a longer alkane-chain bridging group between a chromophoric parent structure and an active group of the dye, which effectively promotes the donating-withdrawing effect on the electron cloud in the conjugated system, enhances the hyperchromic effect, effectively reduce the influence of the active group itself and its reaction on the dye coloring system, improves the color and stability against acid and alkali of the dye, and facilitate the improvement of the compatibility of the dye with supercritical fluid and the dyeing performance for natural fibers as well. The invention also discloses an intermediate of the reactive disperse dye, and a method for preparing the reactive disperse dye.

9 Claims, 2 Drawing Sheets

AZO DYE FOR WATERLESS DYEING OF NATURAL FIBERS IN SUPERCRITICAL $CO_2$ FLUID, AND PREPARATION METHOD THEREOF

This application is the National Stage Application of PCT/CN2018/117077, filed on Nov. 23, 2018, which claims priority to Chinese Patent Application No.: 201811019400.1, filed Sep. 3, 2018, each of which is incorporated by reference for all purposes as if fully set forth herein.

FIELD OF THE INVENTION

The present invention relates to the technical field of reactive disperse dyes, and particularly to a special-purpose azo dye for waterless dyeing of natural fibers in supercritical $CO_2$ fluid, and a preparation method thereof.

DESCRIPTION OF THE RELATED ART

As an environmentally friendly process, supercritical $CO_2$ fluid processing technology has received wide attention in the field of textile dyeing and finishing. Supercritical $CO_2$ fluid not only has the characteristics of low viscosity, high diffusivity, non-toxicity and harmlessness, and environmental protection, but also can realize the recycling of carbon dioxide fluid and dyeing and finishing aids, to effectively solve the problems of high water consumption and large sewage discharge in a traditional dyeing and finishing process (References: Synthesis and Measurement of Solubilities of Reactive Disperse Dyes for Dyeing Cotton Fabrics in Supercritical Carbon Dioxide [J], Industrial and Engineering Chemistry Research, 2014, 53(36): 13862-13870; Supercritical $CO_2$ dyeing [J], Textile Auxiliaries, 2006, 23(4): 10-13; and Dyeing of Textiles in Supercritical Carbon Dioxide[J], Textile Research Journal, 1993, 63(3): 135-142).

Due to the characteristics of supercritical $CO_2$ fluid itself, the use thereof in waterless dyeing and finishing of synthetic fibers is mature. However, the use of supercritical $CO_2$ fluid in the dyeing of natural fibers still has certain limitations. Due to the different structural characteristics and dyeing and finishing principles of natural fibers from those of synthetic fibers, the dyeing process of synthetic fibers in supercritical $CO_2$ fluid cannot be wholly applied to the processing of natural fibers without change. The methods to solve this limitation include modification of the natural fibers; and preparation of a special dye that can complete the dyeing of natural fibers in supercritical $CO_2$ fluid (References: Dyeing of cotton fabric with reactive disperse dye contain acyl fluoride group in supercritical carbon dioxide[J], Dyes and Pigments, 2017, 139:566-574; and Dyeing of natural and synthetic textiles in supercritical carbon dioxide with disperse reactive dyes[J], Journal of Supercritical Fluids, 2007, 40(3):470-476).

The reactive disperse dye is a specially structured dye which can be dissolved in non-polar supercritical $CO_2$ fluid, and react with reactive groups in natural fibers. It is usually prepared by attaching a reactive group to the parent structure of a disperse dye. The dye can not only be applied to the dyeing of natural fibers in supercritical $CO_2$, but also avoid the damage of the original properties of the fibers caused by fiber modification (References: Dyeing and fastness properties of a reactive disperse dye on PET, nylon, silk and N/P fabrics[J], Fibers and Polymers, 2006, 7(2): 174-179; and Dyeing process, DE3906724A1[P], 1990).

With the development of the use of supercritical $CO_2$ fluid technology in natural fiber processing, the research on reactive disperse dyes has also been paid more and more attention, and there are more and more research results available. "Synthesis and characterization of special reactive disperse dyes applicable in supercritical carbon dioxide fluid" (Wei Xiaochen, Master Thesis of Suzhou University, published on Dec. 3, 2015) discloses an intermediate of a special-purpose reactive disperse dye for dyeing in supercritical $CO_2$, and a reactive disperse dye having a structure of Formula (IV). The reactive disperse dye has high coloring intensity, complete color spectrum and bright color, and can be applied to the dyeing of natural fibers in supercritical $CO_2$. However, the structure of the reactive disperse dye is simple, and there are also disadvantages in the structure of undesirable donating/withdrawing effect of the coupling component on the electron cloud in the conjugated system, and potential influence of the active group on the electron cloud density of the parent structure of the dye.

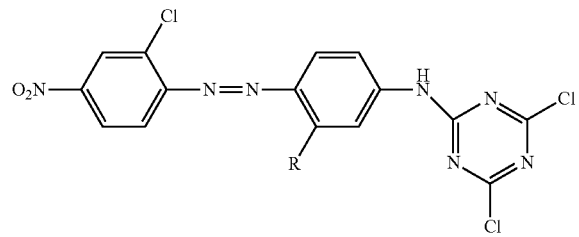

(IV)

SUMMARY OF THE INVENTION

One technical problem to be solved by the present invention is to provide a reactive disperse dye which can effectively reduce the influence of an active group itself and its reaction on the dye coloring system, and an intermediate thereof.

For the above purpose, the invention provides the following technical solutions.

In one aspect, the present invention provides an intermediate of a reactive disperse dye, having a structure of Formula (I):

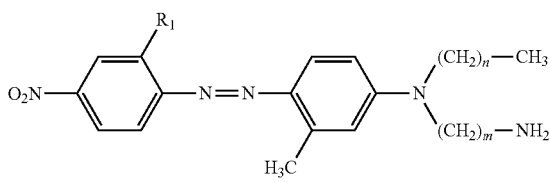

(I)

where $R_1$ is Cl or Br; and in the side-chain substituents of the coupling component, n has a value ranging from $1 \le n \le 6$, for example, the substituent is ethyl when n=1, propyl when n=2, butyl when n=3, and pentyl when n=4, and so on. m has a value ranging from $1 \le m \le 6$, for example, the substituent is 1-aminomethyl when m=1, 2-aminoethyl when m=2, 3-aminopropyl when m=3, and 4-aminobutyl when m=4, and so on.

Preferably, $R_1$ is Cl; n=1, that is, the substituent is ethyl; and m=2, that is, the substituent is 2-aminoethyl.

In another aspect, the present invention also provides a reactive disperse dye, which is directly prepared from the aforementioned dye intermediate, and has a structure of Formula (II):

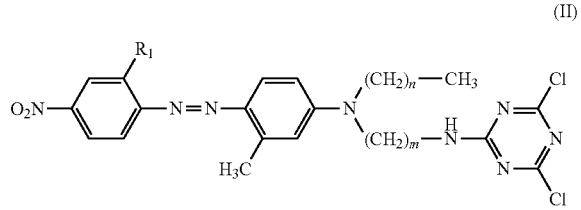

where $R_1$ is Cl or Br; and in the side-chain substituents of the coupling component, n has a value ranging from $1 \leq n \leq 6$, for example, the substituent is ethyl when n=1, propyl when n=2, butyl when n=3, and pentyl when n=4, and so on. m has a value ranging from $1 \leq m \leq 6$, for example, the substituent is 1-aminomethyl when m=1, 2-aminoethyl when m=2, 3-aminopropyl when m=3, and 4-aminobutyl when m=4, and so on.

Preferably, $R_1$ is Cl; n=1, that is, the substituent is ethyl; and m=2, that is, the substituent is 2-aminoethyl.

In a further aspect, the present invention provides a method for preparing the intermediate of the reactive disperse dye, which comprises the following steps:

(1) under an acidic condition, diazotizing 2-chloro-4-nitroaniline or 2-bromo-4-nitroanilineto obtain a diazotized product;

(2) coupling the diazotized product with a coupling component at pH 5-7, to obtain a dye intermediate of Formula (I), where the coupling component has a structure of Formula (III):

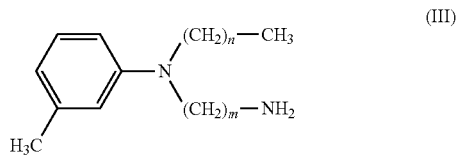

where in the side-chain substituent of the coupling component, m has a value in the range of $1 \leq m \leq 6$, and n has a value in the range of $1 \leq n \leq 6$.

In a preferred embodiment of the present invention, Step (1) specifically comprises: dissolving 2-chloro-4-nitroaniline or 2-bromo-4-nitroaniline in a solvent, controlling the resulting solution to be acidic by adding concentrated hydrochloric acid, and then reacting with sodium nitrite for diazotization.

In Step (1) of the invention, the reaction medium may be adjusted to be acidic with concentrated hydrochloric acid, concentrated sulfuric acid, or acetic acid, and preferably concentrated hydrochloric acid.

In a preferred embodiment of the invention, in Step (1), the solvent comprises an organic solvent and water, and the solvent contains water due to the participation of the water-soluble raw material in the reaction. The organic solvent is selected from the group consisting of N, N-dimethylformamide, 1,4-dioxane, acetic acid and any combination thereof.

In a preferred embodiment of the invention, in Step (1), the volume ratio of the organic solvent to water is 15-10:5-10, and more preferably 5-10:5-10. If the proportion of the organic solvent is too small, the raw material cannot be sufficiently dissolved; and if the ratio is too large, the subsequent separation of the product is more difficult.

In a preferred embodiment of the invention, in Step (1), the diazotization reaction time is 2 to 4 h.

In a preferred embodiment of the invention, in Step (2), before the coupling reaction the method also comprises a step of adding an aqueous urea solution to remove excess nitrous acid, to prevent nitrous acid from affecting the coupling reaction.

In Step (2) of the invention, when the pH is 5-7, the coupling reaction is facilitated, and the pH is preferably 6, at which the coupling reaction proceeds most desirably. Preferably, the pH of the reaction medium is adjusted with a sodium hydroxide solution.

In a preferred embodiment of the invention, in Step (2), the coupling reaction temperature is 0 to 5° C. and the time is 3 to 5 h.

In a preferred embodiment of the invention, the method also comprises a step of purifying the obtained dye intermediate by column chromatography on silica gel, where the silica powder for purification is 200 to 300 mesh; the eluent is petroleum ether, dichloromethane and acetone; and the volume ratio of petroleum ether to dichloromethane is 0-3:1-4, and the volume ratio of acetone to dichloromethane is 0-4:1-4.

In another aspect, the invention also provides a method for preparing the reactive disperse dye, which comprises reacting the dye intermediate of Formula (I) with cyanuric chloride in a solvent in the presence of an acid binding agent, to obtain a reactive disperse dye of Formula (II).

The solvent comprises an organic solvent and water, and the organic solvent is selected the group consisting of N, N-dimethylformamide, 1,4-dioxane, acetic acid and any combination thereof.

In a preferred embodiment of the invention, the acid binding agent is sodium carbonate and/or sodium bicarbonate. During the reaction, the acid binding agent can neutralize acidic byproducts formed in the reaction, so that more target dye can be produced, thereby increasing the yield of the dye.

In a preferred embodiment of the invention, the method also includes a step of purifying the obtained reactive disperse dye by column chromatography on silica gel. Where the silica powder used in the purification is 200 to 300 meshes. The eluent is petroleum ether, dichloromethane and acetone; and the volume ratio of petroleum ether to dichloromethane is 0-3:1-4, and the volume ratio of acetone to dichloromethane is 0-4:1-4.

In a preferred embodiment of the invention, in the preparation of the dye intermediate and the dye, the molar ratio of the aromatic primary amine, concentrated hydrochloric acid, sodium nitrite, coupling component, acid binding agent and cyanuric chloride is 1:10-15:1.1-1.5:1.1-1.5:1-2:1-1.5.

As compared with the prior art, the invention has the following advantages.

The reactive disperse dye of the invention has a longer alkane-chain bridging group between a chromophoric parent structure and a cyanuric chloride active group of the dye, which effectively promotes the donating-withdrawing effect on the electron cloud in the conjugated system, enhances the hyperchromic effect, effectively reduce the influence of the active group itself and its reaction on the dye coloring system, improves the color and stability against acid and alkali of the dye, and facilitates the improvement of the compatibility of the dye with supercritical fluid and the dyeing performance for natural fibers as well.

The reactive disperse dye of the invention is not only suitable for dyeing in a water bath, but also provides a desirable dye for dyeing of natural fibers in supercritical $CO_2$.

The preparation process of the invention has mild conditions, excellent reaction controllability and safe operation, and the production cost is low.

DETAILED DESCRIPTION OF THE PREFERRED EMBODIMENTS

Figure 1:
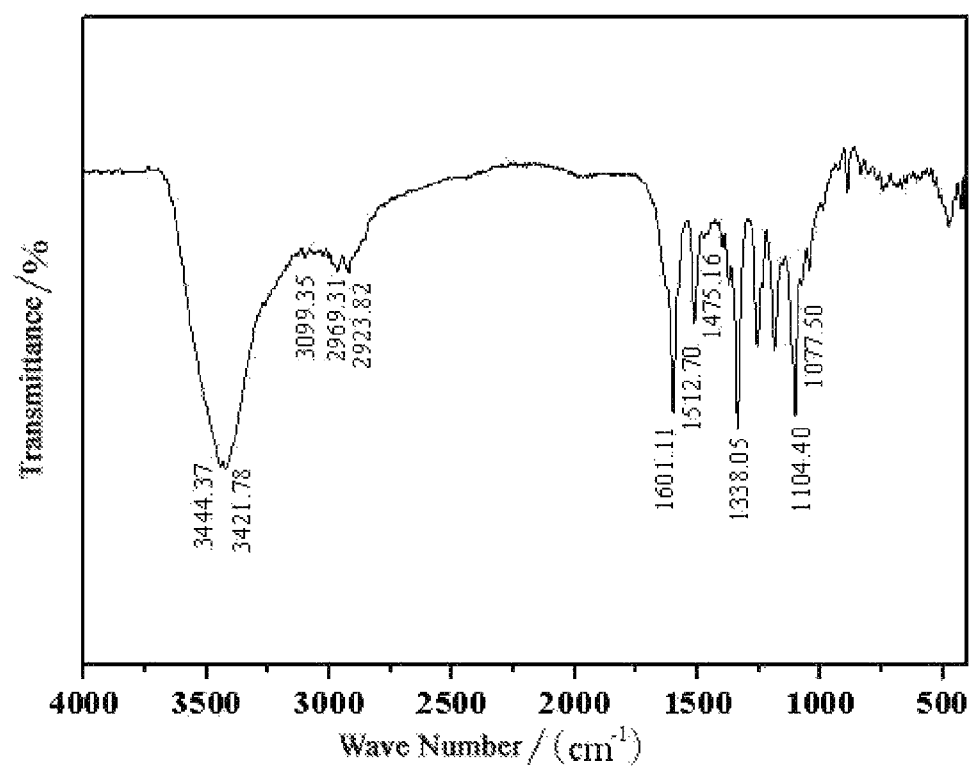
FIG. 1 is a Fourier-transform infrared spectrum of a purified intermediate of a reactive disperse dye according to an embodiment of the invention.

The invention will be further illustrated in more detail with reference to the accompanying drawings and embodiments. It is noted that, the following embodiments only are intended for purposes of illustration, but are not intended to limit the scope of the present invention.

Embodiment 1

Preparation of Dye Intermediate (1) 0.5 mmol of 2-chloro-4-nitroaniline was weighed and placed into a 100 ml three-neck flask, added with 10 ml of N, N-dimethylformamide and 5 ml of deionized water, and ultrasonically dispersed and dissolved. The three-neck flask was placed on a low temperature magnetic stirrer, and stirred evenly at a temperature controlled as 0-5° C. Then, 5 mmol of concentrated hydrochloric acid was added to the system. After the reaction system reached a predetermined temperature range, 5 ml of 0.11 mmol/ml sodium nitrite aqueous solution was slowly added to the system dropwise, and the reaction was continued for 2 h. Then, 5 ml of 0.01 mmol/mL urea solution was added, and fully reacted for 10 min. The reaction product was traced by TLC.

(2) The pH of the diazonium salt reaction system in Step (1) was adjusted to about 6 with a sodium hydroxide solution. 0.55 mmol of a N-(2-aminoethyl)-N-ethyl-m-toluidine solution was taken, dissolved in 5 ml of N, N-dimethylformamide, and then slowly added dropwise to the above diazonium salt solution. The reaction was continued at 0-5° C. for 3 h, and the reaction was traced by TLC. After the reaction was completed, the reaction system was diluted with deionized water, filtered under suction, and washed. The filtrate was extracted with dichloromethane, concentrated by rotary evaporation, and mixed with the filtered product. The mixed product was separated and purified by column chromatography on silica gel to obtain a dye intermediate. The yield is 93.58% and the purity of the product is 99%.

Embodiment 2

Preparation of Dye Intermediate (1) 0.5 mmol of 2-chloro-4-nitroaniline was weighed and placed into a 100 ml three-neck flask, added with 10 ml of 1,4-dioxane and 5 ml of deionized water, and ultrasonically dispersed and dissolved. The three-neck flask was placed on a low temperature magnetic stirrer, and stirred evenly at a temperature controlled as 0-5° C. Then, 5 mmol of concentrated hydrochloric acid was added to the system. After the reaction system reached a predetermined temperature range, 5 ml of 0.11 mmol/ml sodium nitrite aqueous solution was slowly added to the system dropwise, and the reaction was continued for 2 h. Then, 5 ml of 0.01 mmol/mL urea solution was added, and fully reacted for 10 min. The reaction product was traced by TLC.

(2) The pH of the diazonium salt reaction system in Step (1) was adjusted to about 6 with a sodium hydroxide solution. 0.55 mmol of a N-(2-aminoethyl)-N-ethyl-m-toluidine solution was taken, dissolved in 5 ml of 1,4-dioxane, and then slowly added dropwise to the above diazonium salt solution. The reaction was continued at 0-5° C. for 3 h, and the reaction was traced by TLC. After the reaction was completed, the reaction system was diluted with deionized water, filtered under suction, and washed. The filtrate was extracted with dichloromethane, concentrated by rotary evaporation, and mixed with the filtered product. The mixed product was separated and purified by column chromatography on silica gel to obtain a dye intermediate. The yield is 94.19% and the purity of the product is 98%.

Embodiment 3

Preparation of Reactive Disperse Dye (1) 0.05 g (0.138 mmol) of the purified target dye intermediate was weighed and placed into a 100 ml three-neck flask, and ultrasonically dispersed and dissolved in 5 ml of 1,4-dioxane and 5 ml of deionized water. The three-neck flask was placed on a low temperature magnetic stirrer, and stirred evenly at a temperature controlled as 0-5° C. 0.207 mmol of cyanuric chloride and 0.276 mmol of sodium carbonate were dissolved respectively in 5 ml of 1,4-dioxane and 5 ml of deionized water, and then slowly added dropwise to the three-neck flask at the same time. The reaction was continued for 2 h. After the reaction was completed, the reaction system was diluted with deionized water, filtered under suction, and washed. The filtrate was extracted with dichloromethane, concentrated by rotary evaporation, and mixed with the filtered product. The mixed product was separated and purified by column chromatography on silica gel to obtain a dye intermediate. The yield of the final reactive disperse dye is 71.56% and the purity of the product is 99%.

Embodiment 4

Preparation of Reactive Disperse Dye (1) 0.05 g (0.138 mmol) of the purified target dye intermediate was weighed and placed into a 100 ml three-neck flask, and ultrasonically dispersed and dissolved in 5 ml of 1,4-dioxane and 5 ml of deionized water. The three-neck flask was placed on a low temperature magnetic stirrer, and stirred evenly at a temperature controlled as 0-5° C. 0.207 mmol of cyanuric chloride and 0.276 mmol of sodium bicarbonate were dissolved respectively in 5 ml of 1,4-dioxane and 5 ml of deionized water, and then slowly added dropwise to the three-neck flask at the same time. The reaction was continued for 2 h. After the reaction was completed, the reaction system was diluted with deionized water, filtered under suction, and washed. The filtrate was extracted with dichloromethane, concentrated by rotary evaporation, and mixed with the filtered product. The mixed product was separated and purified by column chromatography on silica gel to obtain a dye intermediate. The yield of the final reactive disperse dye is 74.40% and the purity of the product is 99%.

Embodiment 5

Characterization and Performance Test

The purified dye intermediates and reactive disperse dyes obtained in embodiments 1-4 were structurally characterized by Fourier transform IR spectroscopy and UV-Vis absorption spectroscopy. The results are shown in FIGS. 1, 2 and 3.

The test results by Fourier transform IR spectroscopy of the dye intermediates in FIG. 1 show that the absorption peaks at 3444.37 cm$^{-1}$ and 3421.78 cm$^{-1}$ are respectively attributed to the —NH$_2$ anti-symmetric stretching vibration and symmetric stretching vibration, the absorption peak at 3099.35 cm$^{-1}$ is attributed to the C—H stretching vibration on the aryl ring, the absorption peaks at 2969.31 cm$^{-1}$ and 2923.82 cm$^{-1}$ are respectively attributed to the C—H anti-symmetric stretching vibration and symmetric stretching vibration in an alkyl group, the absorption peak at 1601.11 cm$^{-1}$ is attributed to the N=N stretching vibration, the absorption peaks at 1512.70 cm$^{-1}$ and 1338.05 cm$^{-1}$ are respectively attributed to the Ar—NO$_2$ anti-symmetric stretching vibration and symmetric stretching vibration, and the absorption peak at 1104.40 cm$^{-1}$ is attributed to the C—Cl stretching vibration on the aryl ring.

Figure 2:
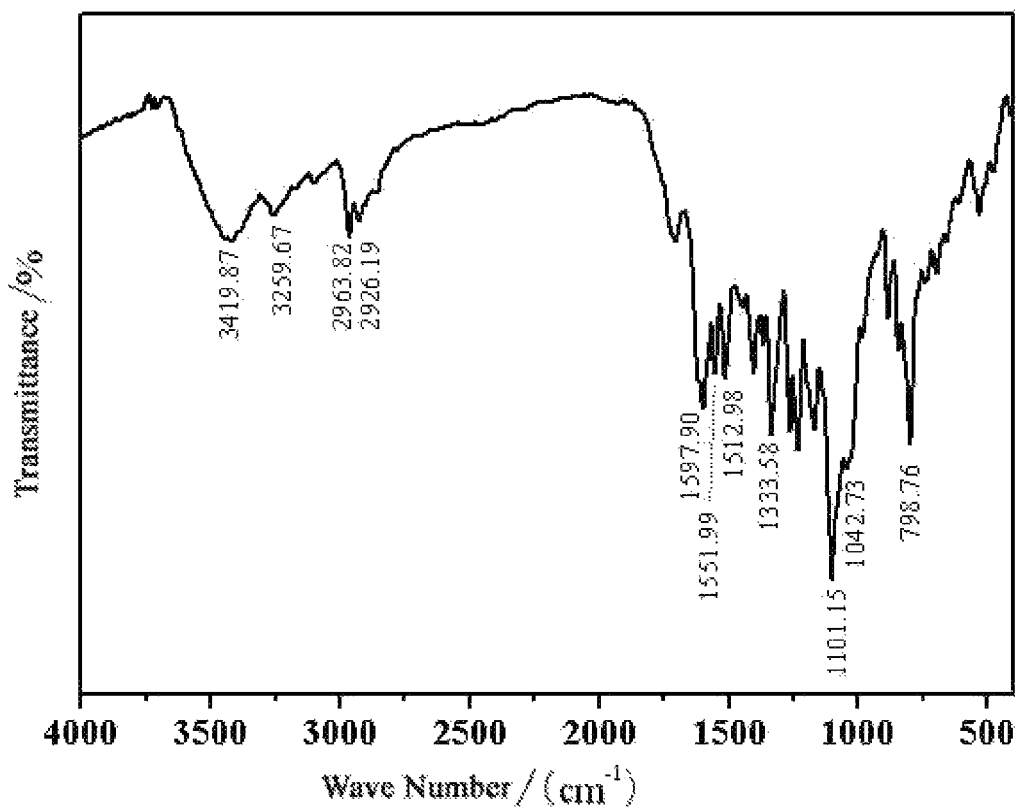
FIG. 2 is a Fourier-transform infrared spectrum of a purified reactive disperse dye according to an embodiment of the invention.
Figure 3:
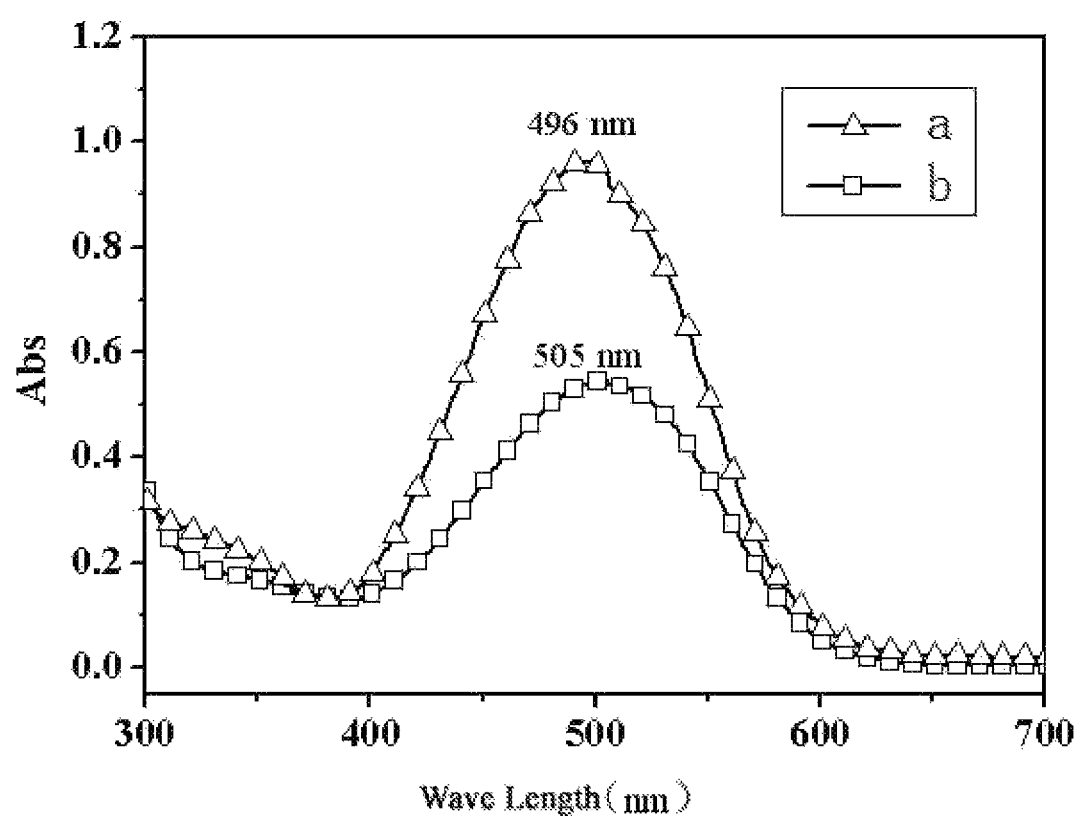
FIG. 3 is a UV-Vis absorption spectrum of a dye intermediate and a reactive disperse dye according to an embodiment of the invention.

The test results by Fourier transform IR spectroscopy of the reactive disperse dyes in FIG. 2 show that the absorption peak at 3419.87 cm$^{-1}$ is attributed to the N—H stretching vibration, the absorption peak at 3259.67 cm$^{-1}$ is attributed to the C—H stretching vibration on the aryl ring, the absorption peaks at 2963.82 cm$^{-1}$ and 2926.19 cm$^{-1}$ are respectively attributed to the C—H anti-symmetric stretching vibration and symmetric stretching vibration in an alkyl group, the absorption peak at 1597.90 cm$^{-1}$ is attributed to the N=N stretching vibration, the absorption peak at 1551.99 cm$^{-1}$ is attributed to the C=N stretching vibration, the absorption peaks at 1512.98 cm$^{-1}$ and 1333.58 cm$^{-1}$ are respectively attributed to the Ar—NO$_2$ anti-symmetric stretching vibration and symmetric stretching vibration, the absorption peak at 1101.15 cm$^{-1}$ is attributed to the C—Cl stretching vibration on the aryl ring, and the absorption peak at 798.76 cm$^{-1}$ is attributed to the C—Cl stretching vibration on the triazine ring.

Comparison of the test results of FIGS. 1 and 2 shows that, the cyanuric chloride reactive group is successfully introduced into the parent structure of the reactive disperse dyes prepared by the present invention.

FIG. 3 is a UV-Vis absorption spectrum of a dye intermediate and a reactive disperse dye in a dichloromethane solution, where curve a is the dye intermediate (in which the maximum absorption wavelength is 496 nm, and the corresponding molar absorption coefficient $\varepsilon_{max}=8.86\times10^3$ L/(mol·cm)), and curve b is the reactive disperse dye (in which the maximum absorption wavelength is 505 nm, and the corresponding molar absorption coefficient $\varepsilon_{max}=5.91\times10^3$ L/(mol·cm)). It can be seen from curves a and b that the variation in the maximum absorption wavelength between the active disperse dye and the dye intermediate in the embodiments of the invention is $\Delta\lambda_{max}=505-496=9$ nm, which is much smaller than the change in the maximum absorption wavelength, $\Delta\lambda_{max}=395-326=69$ nm, described in "Synthesis and characterization of special reactive disperse dyes applicable in supercritical carbon dioxide fluid". The above results indicate that the alkyl bridging group between the reactive group and the parent structure of the dye significantly reduces the influence of the introduced cyanuric cyanide reactive group on the chromophoric parent structure of the dye, and avoid the appreciable change of the main color of the dye caused by the cyanuric cyanide reactive group.

The above description is only preferred embodiments of the present invention and not intended to limit the present invention, it should be noted that those of ordinary skill in the art can further make various modifications and variations without departing from the technical principles of the present invention, and these modifications and variations also should be considered to be within the scope of protection of the present invention.

What is claimed is:

1. A reactive disperse dye, having a structure of Formula (II):

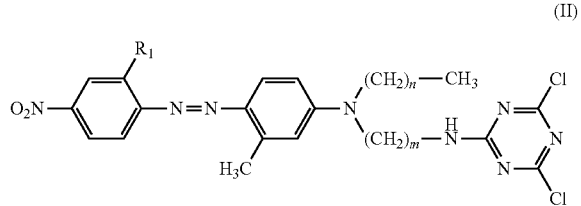

wherein R$_1$ is Cl or Br; and 1≤m≤6, and 1≤n≤6.

2. The reactive disperse dye according to claim 1, wherein R$_1$ is Cl, m=2, and n=1.

3. A method for preparing an intermediate of a reactive disperse dye having a structure of Formula (II),

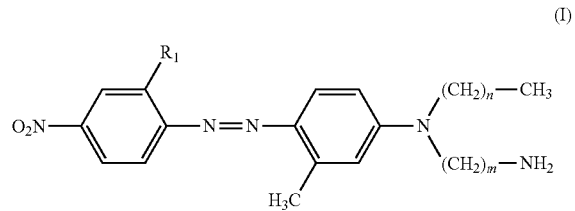

wherein R$_1$ is Cl or Br; and 1≤m≤6, and 1≤n≤6, comprising steps of:
(1) under an acidic condition, diazotizing 2-chloro-4-nitroaniline or 2-bromo-4-nitroaniline to obtain a diazotized product;
(2) coupling the diazotized product with a coupling component at pH 5-7, to obtain a dye intermediate of Formula (I), wherein the coupling component has a structure of Formula (III):

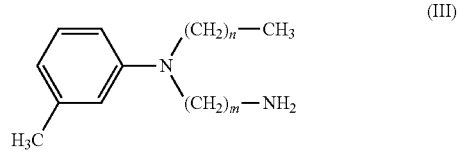

wherein 1≤m≤6 and 1≤n≤6.

4. The method for preparing an intermediate of a reactive disperse dye according to claim 3, wherein Step (1) specifically comprises dissolving 2-chloro-4-nitroaniline or 2-bromo-4-nitroaniline in a mixed solvent of an organic solvent with water, controlling the resulting solution to be acidic by adding concentrated hydrochloric acid, and then adding sodium nitrite for diazotization, to obtain the diazotized product.

5. The method for preparing an intermediate of a reactive disperse dye according to claim 4, wherein the organic solvent is selected from the group consisting of N, N-dimethylformamide, 1,4-dioxane, acetic acid and any combination thereof.

6. The method for preparing an intermediate of a reactive disperse dye according to claim 4, wherein in Step (2), before the coupling reaction the method also comprises adding an aqueous urea solution to remove excess nitrous acid.

7. The method for preparing an intermediate of a reactive disperse dye according to claim 3, wherein in Step (2), the method also comprises purifying the dye intermediate by column chromatography on silica gel, a eluent for column chromatography is petroleum ether, dichloromethane and acetone, and the volume ratio of petroleum ether to dichloromethane being 0-3:1-4, and the volume ratio of acetone to dichloromethane being 0-4:1-4.

8. A method for preparing a reactive disperse dye according to claim 1, comprising reacting the dye intermediate of Formula (I) with cyanuric chloride in a solvent in the presence of an acid binding agent, to obtain a reactive disperse dye of Formula (II),

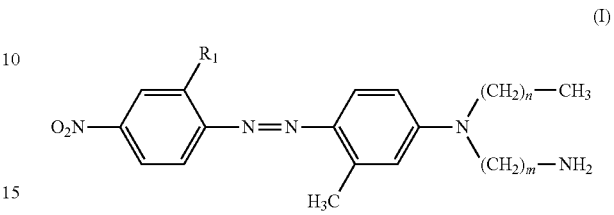

wherein $R_1$ is Cl or Br; and $1 \leq m \leq 6$, and $1 \leq n \leq 6$.

9. The method for preparing a reactive disperse dye according to claim 8, wherein the acid binding agent is sodium carbonate and/or sodium bicarbonate.

* * * * *